United States Patent [19]

Brown

[11] Patent Number: 5,610,148
[45] Date of Patent: Mar. 11, 1997

[54] MACROSCOPICALLY ORIENTED CELL ADHESION PROTEIN FOR WOUND TREATMENT

[75] Inventor: Robert Brown, Middlesex, United Kingdom

[73] Assignee: University College London, United Kingdom

[21] Appl. No.: 416,465

[22] Filed: Apr. 4, 1995

Related U.S. Application Data

[63] Continuation of Ser. No. 87,733, Jul. 16, 1993, abandoned.

[30] Foreign Application Priority Data

Jan. 18, 1991 [GB] United Kingdom .................. 9101191

[51] Int. Cl.$^6$ ..................................................... A61K 38/39
[52] U.S. Cl. .............................. 514/21; 514/12; 530/380; 530/382; 530/383
[58] Field of Search ................................... 530/380, 382, 530/383; 514/12, 21

[56] References Cited

U.S. PATENT DOCUMENTS

| 4,703,108 | 10/1987 | Silver et al. ............................. 530/356 |
| 4,885,295 | 12/1989 | Bell . |
| 4,925,924 | 5/1990 | Silver et al. ............................. 530/356 |
| 4,955,892 | 9/1990 | Daniloff . |
| 4,970,298 | 11/1990 | Silver et al. ............................. 530/356 |
| 4,973,466 | 11/1990 | Reich ..................................... 424/426 |
| 4,983,580 | 1/1991 | Gibson et al. .............................. 514/2 |
| 5,013,732 | 5/1991 | Bell . |
| 5,043,288 | 8/1991 | Motsenbocker . |
| 5,043,429 | 8/1991 | Zimmerman . |
| 5,104,856 | 4/1992 | Esko et al. . |
| 5,120,828 | 6/1992 | Charonis . |
| 5,124,155 | 6/1992 | Reich ..................................... 424/428 |

FOREIGN PATENT DOCUMENTS

| 314109 | 5/1989 | European Pat. Off. . |
| 340628 | 11/1989 | European Pat. Off. . |
| 362526 | 4/1990 | European Pat. Off. . |
| 376189 | 7/1990 | European Pat. Off. . |
| 221977 | 8/1990 | European Pat. Off. . |
| 384362 | 8/1990 | European Pat. Off. . |
| 386906 | 9/1990 | European Pat. Off. . |
| 397633 | 11/1990 | European Pat. Off. . |
| 397635 | 11/1990 | European Pat. Off. . |
| 399806 | 11/1990 | European Pat. Off. . |
| 406428 | 1/1991 | European Pat. Off. . |
| 410006 | 1/1991 | European Pat. Off. . |
| 416250 | 3/1991 | European Pat. Off. . |
| 482649 | 4/1991 | European Pat. Off. . |
| 428266 | 5/1991 | European Pat. Off. . |
| 433817 | 6/1991 | European Pat. Off. . |
| 434836 | 7/1991 | European Pat. Off. . |
| 437622 | 7/1991 | European Pat. Off. . |
| 455263 | 11/1991 | European Pat. Off. . |
| 459577 | 12/1991 | European Pat. Off. . |
| 466505 | 1/1992 | European Pat. Off. . |
| 468181 | 1/1992 | European Pat. Off. . |
| 412951 | 2/1992 | European Pat. Off. . |
| 469985 | 2/1992 | European Pat. Off. . |
| 473564 | 3/1992 | European Pat. Off. . |
| 477833 | 4/1992 | European Pat. Off. . |
| 479071 | 4/1992 | European Pat. Off. . |
| 480189 | 4/1992 | European Pat. Off. . |
| 488258 | 6/1992 | European Pat. Off. . |
| 488583 | 6/1992 | European Pat. Off. . |
| 499544 | 8/1992 | European Pat. Off. . |
| 501233 | 9/1992 | European Pat. Off. . |
| 502496 | 9/1992 | European Pat. Off. . |
| 503301 | 9/1992 | European Pat. Off. . |
| 503583 | 9/1992 | European Pat. Off. . |
| 503646 | 9/1992 | European Pat. Off. . |
| 505749 | 9/1992 | European Pat. Off. . |
| 505868 | 9/1992 | European Pat. Off. . |

(List continued on next page.)

OTHER PUBLICATIONS

Caffesse, R. C. et al., "The effect of citric acid & fibronectin . . . ", J. Clin. Periodontol., vol. 12(7), pp. 578–590, 1985.

Clark, R. A. F, "Fibronectin matrix deposition and fibronectin . . . ", J. Invest. Dermatol., 94/6 Suppl., pp. 128S–134S, 1990.

Grinnell, F et al., "Distribution of Fibronectin during wound . . . ", J. Invest. Dermatol., vol. 76(3), 1981, pp. 181–189.

Baur, Paul et al., "The myofibroblast anchoring strand . . . ", J. Trauma, vol. 23(10), pp. 853–862, 1983.

Caffesse, R. G. et al., J. Clin. Periodontol., vol. 12(7), pp. 578–590, 1985.

Chiquet et al: "Muschle morphogenesis: Evidence for anorganizing function of exogenous fibronectin"; Developmental Biology, vol. 88, No. 2, Dec. 1981, pp. 220–235 (especially p. 230—col. 2—p. 234).

Simmons, "Evaluation of collagen cross–linking techniques for the stabilization of tissue matrices", Biotechnol–Appl–Biochem., 1993 Feb.; 17 (Pt 1):23–9.

Freed, "Survival of implanted fetal dopamine cells and neurologic improvement 12 to 46 months after transplantation for Parkinson's disease", N. Engl. J. Med., 1992 Nov. 26; 327(22):1549–55.

Gershon, "Compliance and ultimate strength of composite arterial prostheses", Biomaterials, 1992; 13(1):38–43.

Ricci, "In–vitro tendon cell growth on synthetic fiber implant materials: biological implications", Bull. Hosp. Jt. Dis. Orthop. Inst., 1990 Fall; 50(2):126–38.

Matsuda, "Development of a novel artificial matrix with cell adhesion peptides for cell culture and artificial and hybrid organs", ASAIO. Trans. 1989 Jul.–Sep.; 35(3):677–9.

Jakobson, "A simple method for shell–less cultivation of chick embryos", Pharmacol–Toxicol. 1989 Feb.; 64(2):193–5.

Brown, "Therapeutic Uses of Cell–Matrix Adhesive Proteins", Current Opinion in Therapeutic Patents, Aug. 1993, pp. 1117–1140.

*Primary Examiner*—Chhaya D. Sayala
*Attorney, Agent, or Firm*—Cushman Darby & Cushman IP Group of Pillsbury Madison & Sutro

[57] ABSTRACT

A porous macroscopically undirectionally oriented cell adhesion protein may be used to promote and direct wound healing.

13 Claims, No Drawings

FOREIGN PATENT DOCUMENTS

| Number | Date | Country |
|---|---|---|
| 507187 | 10/1992 | European Pat. Off. |
| 507604 | 10/1992 | European Pat. Off. |
| 509120 | 10/1992 | European Pat. Off. |
| 509517 | 10/1992 | European Pat. Off. |
| 510483 | 10/1992 | European Pat. Off. |
| 512301 | 11/1992 | European Pat. Off. |
| 512916 | 11/1992 | European Pat. Off. |
| 514721 | 11/1992 | European Pat. Off. |
| 514970 | 11/1992 | European Pat. Off. |
| 517174 | 12/1992 | European Pat. Off. |
| 517182 | 12/1992 | European Pat. Off. |
| 519901 | 12/1992 | European Pat. Off. |
| 522606 | 1/1993 | European Pat. Off. |
| 526756 | 2/1993 | European Pat. Off. |
| 527056 | 2/1993 | European Pat. Off. |
| 529659 | 3/1993 | European Pat. Off. |
| 529858 | 3/1993 | European Pat. Off. |
| 531978 | 3/1993 | European Pat. Off. |
| WO8905342 | 6/1989 | WIPO |
| WO8910135 | 11/1989 | WIPO |
| WO9008833 | 8/1990 | WIPO |
| WO9011365 | 10/1990 | WIPO |
| WO9012033 | 10/1990 | WIPO |
| WO9012580 | 11/1990 | WIPO |
| WO9013306 | 11/1990 | WIPO |
| WO9013566 | 11/1990 | WIPO |
| WO9013644 | 11/1990 | WIPO |
| WO9013647 | 11/1990 | WIPO |
| WO9013653 | 11/1990 | WIPO |
| WO9014418 | 11/1990 | WIPO |
| WO9015620 | 12/1990 | WIPO |
| WO9101380 | 2/1991 | WIPO |
| WO9103252 | 3/1991 | WIPO |
| WO9103559 | 3/1991 | WIPO |
| WO9104058 | 4/1991 | WIPO |
| WO9105048 | 4/1991 | WIPO |
| WO9105566 | 5/1991 | WIPO |
| WO9106315 | 5/1991 | WIPO |
| WO9107974 | 6/1991 | WIPO |
| WO9109122 | 6/1991 | WIPO |
| WO9109614 | 7/1991 | WIPO |
| WO9109874 | 7/1991 | WIPO |
| WO9110683 | 7/1991 | WIPO |
| WO9111462 | 8/1991 | WIPO |
| WO9112026 | 8/1991 | WIPO |
| WO9113085 | 9/1991 | WIPO |
| WO9113093 | 9/1991 | WIPO |
| WO9113152 | 9/1991 | WIPO |
| WO9113625 | 9/1991 | WIPO |
| WO9115224 | 10/1991 | WIPO |
| WO9116633 | 10/1991 | WIPO |
| WO9117248 | 11/1991 | WIPO |
| WO9117444 | 11/1991 | WIPO |
| WO9118639 | 12/1991 | WIPO |
| WO9200092 | 1/1992 | WIPO |
| WO9200751 | 1/1992 | WIPO |
| WO9200995 | 1/1992 | WIPO |
| WO9201049 | 1/1992 | WIPO |
| WO9204442 | 3/1992 | WIPO |
| WO9206196 | 4/1992 | WIPO |
| WO9207870 | 5/1992 | WIPO |
| WO9208464 | 5/1992 | WIPO |
| WO9208472 | 5/1992 | WIPO |
| WO9208476 | 5/1992 | WIPO |
| WO9210199 | 6/1992 | WIPO |
| WO9209200 | 6/1992 | WIPO |
| WO9209268 | 6/1992 | WIPO |
| WO9209293 | 6/1992 | WIPO |
| WO9211367 | 7/1992 | WIPO |
| WO9211866 | 7/1992 | WIPO |
| WO9212119 | 7/1992 | WIPO |
| WO9212236 | 7/1992 | WIPO |
| WO9212727 | 8/1992 | WIPO |
| WO9212729 | 8/1992 | WIPO |
| WO9212994 | 8/1992 | WIPO |
| WO9213003 | 8/1992 | WIPO |
| WO9213887 | 8/1992 | WIPO |
| WO9217065 | 10/1992 | WIPO |
| WO9217187 | 10/1992 | WIPO |
| WO9217188 | 10/1992 | WIPO |
| WO9217192 | 10/1992 | WIPO |
| WO9217206 | 10/1992 | WIPO |
| WO9217498 | 10/1992 | WIPO |
| WO9217499 | 10/1992 | WIPO |
| WO9217569 | 10/1992 | WIPO |
| WO9217604 | 10/1992 | WIPO |
| WO9218160 | 10/1992 | WIPO |
| WO9218543 | 10/1992 | WIPO |
| WO9218610 | 10/1992 | WIPO |
| WO9218643 | 10/1992 | WIPO |
| WO9219243 | 11/1992 | WIPO |
| WO9219269 | 11/1992 | WIPO |
| WO9219646 | 11/1992 | WIPO |
| WO9219647 | 11/1992 | WIPO |
| WO9220337 | 11/1992 | WIPO |
| WO9220712 | 11/1992 | WIPO |
| WO9220716 | 11/1992 | WIPO |
| WO9221240 | 12/1992 | WIPO |
| WO9221363 | 12/1992 | WIPO |
| WO9222312 | 12/1992 | WIPO |
| WO9222323 | 12/1992 | WIPO |
| WO9222580 | 12/1992 | WIPO |
| WO9222585 | 12/1992 | WIPO |
| WO9300107 | 1/1993 | WIPO |
| WO9300111 | 1/1993 | WIPO |
| WO9300356 | 1/1993 | WIPO |
| WO9300357 | 1/1993 | WIPO |
| WO9300358 | 1/1993 | WIPO |
| WO9300438 | 1/1993 | WIPO |
| WO9300908 | 1/1993 | WIPO |
| WO9300919 | 1/1993 | WIPO |
| WO9302191 | 2/1993 | WIPO |
| WO9302698 | 2/1993 | WIPO |
| WO9305067 | 3/1993 | WIPO |
| WO9305150 | 3/1993 | WIPO |
| WO9305167 | 3/1993 | WIPO |
| WO9305792 | 4/1993 | WIPO |
| WO9313129 | 7/1993 | WIPO |
| WO9314782 | 8/1993 | WIPO |
| WO9315203 | 8/1993 | WIPO |
| WO9319769 | 10/1993 | WIPO |
| WO9320202 | 10/1993 | WIPO |
| WO9319783 | 10/1993 | WIPO |

MACROSCOPICALLY ORIENTED CELL ADHESION PROTEIN FOR WOUND TREATMENT

This is a continuation of application No. 08/087,733, filed on Jul. 16, 1993, now abandoned.

The present invention relates to materials for use in promoting wound healing, to processes for their production and their use in treating wounds in humans and animals.

There are four stages which can usually be identified in the natural healing process. Initially the wound is closed so as to limit blood loss and prevent infection. Then damaged tissue is removed and pathogens destroyed by phagocytosis. This is followed by granulation in which the wound is invaded by cell types appropriate to the surrounding tissue and scar formation occurs. Finally the scar tissue is remodelled and changes in the cell population occur resulting in a mature, healed wound. In any particular case variations from this general pattern will occur owing to factors such as the site and type of wound and the condition of the patient, and the details of the process, particularly the later stages are, as yet, not well understood.

Although very effective in most cases, the natural wound healing process can fail on occasion, or may be unsatisfactory, and medical intervention is desirable. Typical examples of failure include cases of severe burns involving substantial tissue damage where the wounds often do not even close completely and where skin grafts are required to secure granulation, cases of leg ulcers where, even when the wounds heal, the healed scar is physically weak and liable to break open very easily and cases where, although a wound would heal naturally, the scarring that remains may be unsightly or cause discomfort. Other wounds which frequently require intervention are serious bone fractures and wounds to cartilage, ligaments and tendons which heal slowly or not at all or where the healed wound will not be sufficiently strong.

Despite considerable work over many years there have been no completely satisfactory treatments for many of these problems in wound healing.

The present inventors have developed macroscopically oriented materials, comprising a cell adhesion protein such as fibronectin, which, surprisingly have been shown to promote wound healing, in particular by creating a scaffolding to which the invading cells can adhere thus facilitating this stage of the wound healing procedure. Moreover, by aligning these materials with features of the wound or surrounding tissue, cell invasion may be directed along desired orientations thereby strengthening the initial repair and reducing the amount of reorientation required during the remodelling stage. Thus wound healing may be promoted and the mature healed wound can be made stronger or more cosmetically acceptable or both.

It is the orientation of the cell adhesion protein molecules on a macroscopic scale which is critical to the success of the materials of the invention in directing the wound healing process. In the past, investigations have been made using non-porous fibronectin obtained by precipitation from solution, however this results in at best very small scale orientation of fibronectin molecules and, usually, random orientation thereof, and such materials have no application in directing wound healing in accordance with the present invention.

The present invention therefore provides porous macroscopically oriented cell adhesion protein. Cell adhesion proteins useful in the present invention include fibronectin, vitronectin and von Willebrand protein (also called von Willebrand factor). Fibronectin is the preferred cell adhesion protein.

The invention further provides porous macroscopically oriented cell adhesion protein for use in methods of surgery or therapy practised on the human or animal body. The invention further provides the use of porous macroscopically oriented cell adhesion protein in the manufacture of medicaments, dressings or devices for use in methods of surgery or therapy practiced on the human or animal body. In particular aspects the methods of surgery or therapy involve promoting wound healing or directing wound healing or improving the appearance or strength of a healed wound or any combination of two or more thereof. The method of surgery or therapy may alternatively involve the growth of autograft material such as skin or ligament promoted or directed by porous macroscopically oriented cell adhesion protein.

The present invention also provides a method of treatment of a wounded human or animal comprising applying an effective non-toxic amount of porous macroscopically oriented cell adhesion protein to the wound.

The macroscopically oriented cell adhesion protein of the invention comprises large scale aggregates of cell adhesion protein, which self-assemble under favourable conditions as fibrils, the molecules in each individual fibril lying substantially parallel to each other, each individual fibril being oriented over a distance of at least 100 μm and the fibrils being oriented substantially parallel to each other over macroscopic distances such as at least 0.1 mm, preferably 0.5 and most preferably for at least 1 mm. Individual fibrils may show orientation over a considerable distance, for instance up to 0.5 mm, possibly up to 1 mm or even for 5 mm or more, for instance 1,2,3 or 5 cm. The aggregate of fibrils may be oriented for over 5 mm or 1 cm or more, for instance 2,3, or 5 cm and, when prepared as a continuous web for subsequent division into individual dressings, the aggregate may be oriented over distances of many centimeters or even many meters.

In a simple embodiment of the invention the fibrils are oriented in a single direction and form a sheet or mat, possibly on a substrate for support, which may be applied to a wound. In more complex embodiments such sheets or mats may be laminated in non-parallel directions, for instance with the fibrils of one layer oriented at 90° to fibrils in a second layer. The fibrils may be arranged into fibres or may be formed on a substrate or oriented by fibres of a substrate, and such fibres may be formed into woven and non-woven webs having at least one and often two or more orientation directions. When the oriented materials are formed by coating on a substrate, preferably the substrate will be a biodegradable or resorbable material such that it may be left in the wound and will eventually be destroyed as the wound heals or once it has healed or the substrate may be a physical support which is removed after formation of the oriented material.

In use the materials of the invention may be applied to wounds to direct and promote the cell invasion and thereby to increase the strength, cosmetic acceptability, healing time or other desirable characteristic of the healed wound. By way of example a simple unidirectionally oriented mat may be used with the orientation direction across the width of a linear wound in order to promote the closing of the wound and enhance the resistance to re-opening of the wound. In another example, more complex webs having multiple orientation directions may be used to promote regrowth of damaged tendons, intervertebral discs and corneas whilst directing adoption by the invading cells of orientations matched to that of the surrounding undamaged tissue or to recreate orientations of the original damaged tissue. Thus the use of the oriented materials of the invention will often involve aligning one or more orientation directions of the material with respect to features of the wound or surrounding tissues.

A particular application of the materials of the invention is in stimulation of new capillary growth, a frequently perceived objective for many forms of wound repair. Classically, the approach has been to attempt to stimulate angiogenesis generally, using a diffusible factor. However, one part of the process of angiogenesis is endothelial cell adhesion to and migration over the substrate matrix. A development of the present invention can be applied to this by promoting attachment/migration of capillary cells to discrete fibres or strands. These strands would be orientated in the direction of the required capillary growth. Strands can take the form of (i) pure fibronectin in macroscopic fibrous form; (ii) oriented fibronectin strands laid into conventional wound implant materials (e.g. gelatin or modified cellulose sponges); (iii) oriented fibronectin coated on braided resorbable sutures. Whether formed of oriented Fn or fibronectin coated, the individual strands should be less than 200 μm wide (ideally between 1 and 100 μm). These structures form excellent support and adhesion substrates for repair cells In a further modification (particularly of the Fn-coated, braided suture) it is possible to incorporate a chemotactic stimulus by attaching a solid, growth factor containing gel to one end of the suture. A natural example of such a "gel" would be a blood or plasma clot (ideally prepared from the patient's own blood). Artificial substrates based on gelatin (or other gel-forming material) containing the required angiogenic factor could also be used. This suture would be drawn through or across the damaged tissue in such a way that new vessels would grow towards the end bearing the gel or clot. This form of suture may usefully be employed as an "angiogenic track" during repair of avascular or poorly vascular tissues such as torn menisci, ligaments or tendons.

Fibronectin for use in accordance with the invention may be obtained commercially in non-oriented form and may be oriented by processes such as are described below. Preferably substantially pure fibronectin is used. Other cell adhesion proteins are well known in the literature; again these are available in non-oriented form and require processing for instance as described below. The materials of the invention will usually be provided in sterile, pyrogen-free form.

Oriented materials according to the invention may further comprise additional therapeutic agents, for instance agents which promote wound healing such as growth factors and growth hormones, clotting factors, platelet adhesion promoters such as thrombin, agents which promote calcification, collagen, fibrinogen, antimicrobial agents and heparin.

The fibrils and oriented materials may be used as formed or stabilised by cross-linking using chemical reagents such as glutaraldehyde or enzymes such as factor XIIIa, which is a transglutaminase. Cross-linking with other components such as collagen and fibrinogen, for instance using a transglutaminase, is also contemplated. Where the materials of the invention include collagen and/or fibrinogen it is preferred for these also to be oriented substantially parallel to the fibrils of cell adhesion protein.

Preferably the oriented materials of the invention are used as, or as part of, a wound dressing, or are applied to open wounds separately from a conventional dressing. To derive improved strength and/or cosmetic acceptability of the mature wound it is preferred that the oriented materials are applied to the wound with an orientation direction aligned with features of the surrounding tissues so as to encourage invasion along the orientation direction. For instance, the fibres may be aligned with muscle fibres in the wound or underlying tissue, across a linear wound or parallel with or at right angles to directions in which a tissue will be strained once healed.

The invention further provides a process for producing porous macroscopically oriented cell adhesion protein materials which process comprises forming and orienting cell adhesion protein fibrils from solution and removing the solvent.

Solvents useful in accordance with the present process are generally aqueous solvents such as buffered water, distilled water, demineralised water and pyrogen-free water. The solvent may contain additional solutes and/or suspended particles for inclusion in or deposition on the fibronectin materials.

The solvent may be removed by evaporation, filtration concentration or by aggregating or precipitating the fibronectin using, for instance, appropriate concentrations of salts or by adjusting the pH of the solution to acidic or basic pH and collecting and drying the aggregate or precipitate. The oriented materials are preferably washed and dried and may be optionally stabilised, for instance by chemical cross-linking using reagents such as glutaraldehyde or enzymatically using factor XIIIa.

The cell adhesion protein may be oriented by self-association from solution, preferably a high concentration solution at 0.7 mg/ml or greater, for instance greater than 1 mg/ml, such as at least 1.5 mg/ml, for instance 2 mg/ml or more or even up to 3 mg/ml or more at about neutral pH to form fibrils on solid surfaces which fibrils are sufficiently stable to be handled, recovered and dried. Use of a solution at about 1.5 mg/ml is most preferred. A pH of about 7.6, eg using tris-HCl buffer has been found convenient. Preferably the solution contains soluble ionic compounds to increase the ionic strength thereof, especially in the range up to 0.5 M ionic strength. Preferably the solution also contains urea at preferably 1 to 3 M. A combination of fibronectin, urea at 2 M and 0.1 to 0.5 M sodium chloride is preferred. Thus, for example, fibronectin may be oriented by applying continuous unidirectional motion, such as by stirring, to a saturated solution and removing the solvent so as to aggregate oriented fibronectin, for instance on the stirrer. This may be recovered and blotted to form mats which may be laminated in parallel or non-parallel directions to form a lattice. Alternatively, high concentration solutions may be drawn into fibres and the solvent removed leaving fibronectin fibres comprising oriented fibrils. A preferred technique for drawing fibres involves dipping an applicator onto the surface of the solution and lifting the applicator to produce one or more fibres under the effects of surface tension. A preferred material for the applicator is the mineral mica. In a further alternative, a concentrated solution of fibronectin is applied to a fibrous substrate and the solvent is removed.

Heparin can be incorporated into the fibronectin solution (preferably at ratios of 1:5 to 1:100, by weight heparin: Fn) without impairing its ability to form strands. However, after drying, strands made with higher heparin ratios (e.g. 1:5, heparin:Fn) were flat, with very little mass as a result of the high level of hydration of the newly formed strands due to the heparin content.

The invention will now be illustrated by the following Examples which are not intended to limit the scope of protection in any way.

EXAMPLE 1

A solution of human plasma fibronectin purified by gelatin affinity chromatography (approx 1.0 (eg 0.5 to 1.5)

mg/ml) in neutral pH buffer (10 mM phosphate or 20 mM Tris HCl pH7.5) containing 0.15 M sodium chloride is placed into a pressurized "stirred cell" concentration device with an ultra filtration membrane (molecular weight cut off approx. 10 to 20,000 Daltons: eg Amicon PM 10 membrane). Such a stirred cell (eg 100 ml capacity) is operated at a preferred pressure of 25 psi (range approx. 10 to 75 psi) under nitrogen or under air with a stirring race of approx 300 rpm (range 50 to 600 rpm) at 4° C. The volume is slowly reduced under these conditions to less than half the initial volume giving a fibronectin concentration within the cell of approx 3 mg/ml (range of 2.0 to 10 mg/ml). The conditions for self-aggregation will vary depending on the purity and integrity of the fibronectin starting material, but within these ranges, a large clot or mat of solid fibronectin will be formed on the stirring bar of the cell. This can be removed and fresh fibronectin solution added to permit the formation of more fibronectin matting.

EXAMPLE 2

A starting solution as described in Example 1 but containing over 1 mg/ml of fibronectin (Fn) at a pH around neutrality and sodium chloride concentration up to 0.2 M is prepared. A suitable flat edged "applicator" (for example a 2 cm glass cover slip) is dipped into the solution to a depth of at least 3 mm. This same wetted edge is now touched onto a hydrophilic surface (e.g. flat plastic culture dish) forming a small pool of the Fn solution, clinging to both the "applicator" and the surface. When the applicator is slowly lifted off the surface to be coated, a single strand of protein forms between the "applicator" and "surface" under the effect of surface tension. This strand of protein (spanning between surface and applicator) can be pulled across the surface for 2 to 5 mm and re-attached to the surface by again touching the applicator and the surface. The resultant strand of protein is firmly attached to the surface by multiple subdivided fibrils at either end. They are commonly 2 to 5 µm in diameter and up to 5 mm long. They are stable with or without chemical cross linking (e.g. with glutaraldehyde) and can be washed and dried without becoming dislodged. Their orientation on the "surface" can be controlled precisely.

In cell culture tests, strands of pure fibronectin promoted a directional orientation and attachment of fibroblasts in spite of the presence of soluble fibronectin. Stands of fibronectin were still visible in such cultures after 24 hrs exposure to fibroblasts.

EXAMPLE 3

Mats were prepared as described in Example 1 using a stirred cell, under a range of conditions to test for preferred composition of the starting fibronectin solution. Mat formation was assessed on the basis of the dry weight of mat recovered and uv absorbance (at 280 nm) of the fibronectin solution at the start and end of the mat forming process. Fibronectin solutions made to 2 M with urea were found to be preferable, giving a greater % mat formation at the same ionic strength.

The ionic strength of the Fn solution was raised in increments, using greater concentrations of sodium chloride from zero to 1.0 M, and the recovery of Fn as a mat (as % of total Fn in solution) was measured. From data on the relationship of sodium chloride concentration to % Fn incorporation to the mat, it is clear that mat formation is adequate between 0.1 M and 0.5 M sodium chloride with a preferred concentration of 0.1 M sodium chloride.

EXAMPLE 4

The influence of heparin, in the starting solution of Fn, was tested on the quantity and quality of mats formed in the "stirred cell" (see Example 1). As in Example 3, the efficiency of mat production was measured as % Fn incorporated into the aggregate. Heparin was added to known concentrations of Fn solution at ratios (weight:weight) from 1:15 to 1:200 (heparin:Fn). Heparin was from the Sigma Chemical Co., Poole, Dorset, U.K. Each mat was made under otherwise identical conditions, from solutions of Fn containing 0.1 M sodium chloride, 2 m urea, 50 mM tris-HCl pH7.6. At ratios below 1:15 (Heparin:Fn) mat formation was largely or wholly inhibited. Beyond a ratio of 1:40 there was little change. The preferred ratio is 1:20 to 1:40. Heparin incorporation into the mat (measured by the "Methylene Blue" assay for glycosaminoglycans) was determined at approx. 20 µg/mg of Fn, using a starting solution Heparin:Fn ration of 1:15. This represents an incorporation rate of 30%. In general mats containing heparin had a poorer orientation than those prepared without. All of these materials, when dried, were convenient materials to place into wounds in a variety of tissues, rehydrating to form solid proteinaceous deposits in solutions at physiological ionic strength and pH.

I claim:

1. A method of treating a wound comprising applying an effective, non-toxic amount of a porous macroscopically unidirectionally oriented cell adhesion protein selected from the group consisting of fibronectin, vitronectin and von Willebrand protein to the wound, in which fibrils of the cell adhesion protein are macroscopically unidirectionally oriented.

2. A method according to claim 1 for treating a wound so as to promote wound healing, to direct wound healing, to improve the strength of the wound when healed or to improve the appearance of the wound when healed.

3. A process for producing a porous macroscopically unidirectionally oriented cell adhesion protein selected from the group consisting of fibronectin, vitronectin and von Willebrand protein which process comprises forming and orienting cell adhesion protein fibrils from an aqueous solution thereof by applying continuous unidirectional motion and removing the solvent.

4. A process according to claim 3, wherein the concentration of the aqueous solution of cell adhesion protein is at least 0.7 mg/ml.

5. A wound dressing comprising a porous macroscopically unidirectionally oriented cell adhesion protein selected from the group consisting of fibronectin, vitronectin and von Willebrand protein, in which fibrils of the cell adhesion protein are macroscopically unidirectionally oriented.

6. A wound dressing comprising a porous macroscopically unidirectionally oriented cell adhesion protein selected from the group consisting of fibronectin, vitronectin and von Willebrand protein, in which fibrils of the cell adhesion protein are macroscopically unidirectionally oriented, which wound dressing has two or more non-parallel orientation directions.

7. A method of treating a wound, comprising the steps of:
   a) applying a non-toxic amount of a porous macroscopically unidirectionally oriented cell adhesion protein selected from the group consisting of fibronectin, vitronectin and von Willebrand protein in which fibrils of the cell adhesion protein are macroscopically unidirectionally oriented to the wound and b) allowing the wound to heal while in contact with said macroscopically unidirectionally oriented cell adhesion protein in order to promote wound healing, direct wound healing or improve the appearance or strength of a healed wound.

8. A method of treating a wound, comprising the steps of:

a) applying a non-toxic amount of a porous macroscopically unidirectionally oriented cell adhesion protein selected from the group consisting of fibronectin, vitronectin and von Willebrand protein in which fibrils of the cell adhesion protein are macroscopically unidirectionally oriented to the wound and b) allowing the growth of autograft material promoted or directed by said macroscopically unidirectionally oriented cell adhesion protein.

9. A porous, macroscopically unidirectionally oriented cell adhesion protein, which is selected from the group consisting of fibronectin, vitronectin and von Willebrand protein, in which fibrils of the cell adhesion are macroscopically unidirectionally oriented.

10. The porous macroscopically unidirectionally oriented cell adhesion protein of claim 9 further comprising a therapeutic agent.

11. The porous macroscopically unidirectionally oriented cell adhesion protein of claim 10 wherein the therapeutic agent is one which promotes wound healing.

12. The porous macroscopically unidirectionally oriented cell adhesion protein of claim 11 wherein the therapeutic agent which promotes wound healing is a growth factor.

13. A protein according to claim 9 which is fibronectin.

* * * * *

UNITED STATES PATENT AND TRADEMARK OFFICE
CERTIFICATE OF CORRECTION

PATENT NO. : 5,610,148
DATED : March 11, 1997
INVENTOR(S) : Robert Brown

It is certified that error appears in the above-indentified patent and that said Letters Patent is hereby corrected as shown below:

On the title page, item [63], should read — Continuation of application No. 08/087,733, abandoned, filed as application No. PCT/GB92/00100, Jan. 17, 1992 --

Signed and Sealed this

Seventh Day of July, 1998

Attest:

Attesting Officer

BRUCE LEHMAN

Commissioner of Patents and Trademarks